United States Patent [19]
Stjernfelt et al.

[11] Patent Number: 5,830,865
[45] Date of Patent: Nov. 3, 1998

[54] STORAGE STABLE WATER SOLUTION FOR INFUSION CONTAINING A THROMBIN INHIBITOR

[75] Inventors: Ulla Stjernfelt, Mölndal; Mats Sundgren, Kållered, both of Sweden

[73] Assignee: Astra Aktiebolag, Sodertalje, Sweden

[21] Appl. No.: 557,189

[22] PCT Filed: Oct. 19, 1995

[86] PCT No.: PCT/SE95/01228

§ 371 Date: Dec. 18, 1995

§ 102(e) Date: Dec. 18, 1995

[87] PCT Pub. No.: WO95/14084

PCT Pub. Date: May 17, 1996

[30] Foreign Application Priority Data

Nov. 8, 1994 [SE] Sweden .................................. 9403831

[51] Int. Cl.⁶ .................................................. A61K 47/42
[52] U.S. Cl. ............................................ 514/18; 530/331
[58] Field of Search ...................... 530/326, 331; 514/18

[56] References Cited

U.S. PATENT DOCUMENTS 5,466,131  11/1995  Maraganore ............................. 530/326

FOREIGN PATENT DOCUMENTS 9311152  6/1993  WIPO .

OTHER PUBLICATIONS

WO 94/29336; Antonsson et al., Abstract, in WPI database, entry No. 95–036397/05, Dec. 1994.

*Primary Examiner*—Scott W. Houtteman
*Attorney, Agent, or Firm*—Nixon & Vanderhye

[57] ABSTRACT

This invention relates to a storage stable concentrated water-solution for infusion having a pH in the range from 1.0 to 2.5 and containing an active thrombin inhibitor having the formula $$HOOC\text{-}CH_2\text{-}Y$$

wherein Y is (R)-Cha-Pic-Nag or (R)-Cgl-Aze-Pab, as a salt or as a free base thereof, a process for their preparation and to a method for treatment of a patient in need of said formulation.

17 Claims, No Drawings

STORAGE STABLE WATER SOLUTION FOR INFUSION CONTAINING A THROMBIN INHIBITOR

FIELD OF THE INVENTION

The present invention relates to a new improved storage stable intravenous formulation for infusion of thrombin inhibitors, especially of the peptidic thrombin inhibitors HOOC-CH2-(R)Cha-Pic-Nag and HOOC-CH2-(R)Cgl-Aze-Pab, respectively, to a process for the preparation of said formulation and to a method for treatment by administration of said formulations.

BACKGROUND OF THE INVENTION

Thrombin inhibitors are expected to be effective drugs in a number of diseases characterised by hypercoagulation. Their therapeutic use will be facilitated if stable formulations are available, i.e. formulations having a long shelf-life when stored at room-temperature.

In WO 93/11152, Example P1, a water solution for parenteral administration is disclosed, said formulation is an acetate buffer-solution of HOOC-$CH_2$-(R)Cha-Pic-Nag ×2HBr for parenteral use of pH 3–7, which is within the physiologically acceptable pH range suitable for injections directly into the human body. This solution also includes additives such as sodium chloride to get an isotonic solution.

The active compound HOOC-$CH_2$-(R)-Cgl-Aze-Pab is disclosed in PCT/SE94/00535, filed 2 Jun. 1994 now WO 94/29336, published Dec. 22, 1994. Example P2 in this document describes a solution for parenteral administration, namely a water solution of an active compound and sodium chloride, which is adjusted with NaOH to pH 3–9, preferably 5–7.

The stability of peptides is generally a problem in the pharmaceutical industry. Pharmaceutical formulations, especially with a low concentration of peptides, often loose activity during storage.

Each peptide is different with regard to pharmacological properties. When preparing a pharmaceutical formulation of a specific peptide, consideration can not only be taken to the pharmacological properties of the peptide but also other aspects must be considered such as the industrial manufacture, easy and convenient storage and handling for the hospital staff and safety for the patient. The results of these aspects are not predictable when testing different formulations and each peptide often has a unique solution regarding stability.

It is well known that peptides generally are more susceptible to degradation in an acidic or basic environment than in a neutral solution. However, unexpectedly it has been found that for the peptidic thrombin inhibitors HOOC-$CH_2$-(R)-Cha-Pic-Nag and HOOC-CH2-(R)Cgl-Aze-Pab their storage stability is improved in acidic aqueous solutions.

DISCLOSURE OF THE INVENTION

The scope of the present invention is a storage stable concentrated, water solution for intraveneous infusion of an active thrombin inhibitor the formula

HOOC-$CH_2$-Y wherein Y is (R)-Cha-Pic-Nag or (R)-Cgl-Aze-Pab and having a pH in the range from 1.0 to 2.5, which solution does not require special storage conditions but can be stored at room temperature, i.e. between 15°–30° C., preferably between 18°–28° C., tentatively 25° C.

Thus, the stable water solution of the present invention which is a concentrated water solution of a thrombin inhibitor, is adjusted with a physiologically acceptable organic or inorganic acid, preferably an inorganic mineral acid such as hydrochloric acid, hydrobromic acid etc., for obtaining the desired pH. The hydrochloric acid is most particularly preferred. The formulation is a straight forward one without any stabilising additives.

In an acidic solution the solubility of the two different drugs, respectively, increases and a more concentrated solution can be produced, which means that small containers which are easy to handle can be used.

It is of importance that the pharmaceutical formulation is easy to handle and to dose. Therefore said formulation suitably should be provided in containers intended for parenteral use, such as plastic or glass containers, e.g. vials, ampoules or prefilled syringes, and be added to infusion bags or bottles i.e. the storage stable concentrated water solution must be diluted before the administration to the patients.

An additional improvement is that the solutions do not require additives such as buffer salts, isotonic salts or co-solvents for stability reasons. However, the stable solution may also contain preservatives, i.e. in order to prevent microbiological growth. The solution is aimed to be added to a solution for intravenous infusion such as physiological saline or other electrolytes, glucose, mannitol, dextran etc. or a combination thereof, and parenterally administered.

The solution may be manufactured with the active peptidic thrombin inhibitors HOOC-$CH_2$-(R)-Cha-Pic-Nag and HOOC-$CH_2$-(R)Cgl-Aze-Pab, respectively as commonly used salts or in their base form.

The solution of the present invention will be stable enough to permit room temperature storage for extended periods. A commercial product should preferably have an storage period of at least two years, at the end of which period at least 95% of the active compound should remain, that is the total amount of degradation products should be less than 5%.

The preferred concentrations of HOOC-$CH_2$-(R)-Cha-Pic-Nag may vary within broad ranges between 0.001–200 mg/ml, preferably 0.1–100 mg/ml, more particularly preferred 10–100 mg/ml. The preferred concentrations of HOOC-$CH_2$-(R)Cgl-Aze-Pab may vary within broad ranges between 0.001–300 mg/ml, preferably 0.1–200 mg/ml, more particularly preferred 1–100 mg/ml.

This invention also relates to a process for the preparation of a storage stable water solution, which comprises dissolving in water the active thrombin inhibitors HOOC-$CH_2$-(R) Cha-Pic-Nag or HOOC-CH2-(R)Cgl-Aze-Pab, respectively, adjusting the pH of the obtained solution from 1.0 to 2.5, preferably from 1.5 to 2.0, or to a specific desired value, e.g. 1.0, 1.5, 2.0, 2.5. Suitable volumes when using ampoules, vials or syringes are 0.1–100 ml, preferably 1–10 ml.

The two active thrombin inhibitors, HOOC-$CH_2$-(R)Cha-Pic-Nag and HOOC-$CH_2$-(R)Cgl-Aze-Pab, respectively, are both possible to dissolve in water at room temperature.

EXAMPLES

Analytical methods used in the examples below

Stability assay

A stability indicating method using reversed-phase liquid chromatography in an ion-pair mode and UV-detection at 210 and 238 nm was developed for HOOC-CH2-(R)Cha-Pic-Nag and HOOC-CH2-(R)Cgl -Aze-Pab, respectively.

A standard solution of thrombin inhibitors, 0.018–0.022 mg/mL was prepared, in mobile phase. The sample solution was diluted to a concentration of about 0.02 mg/ml with mobile phase. The column was equilibrated with mobile phase until a stable baseline was obtained. The standard and sample were injected at suitable intervals. The retention time for the active thrombin inhibitors HOOC-CH$_2$-(R)Cha-Pic-Nag and HOOC-CH2-(R)Cgl-Aze-Pab are about 4 and 12 minutes for the methods, respectively.

pH

The pH of the solutions was measured potentiometrically without prior dilution using a Radiometer PHM Reference pH meter with a glass electrode (GK2401C electrode).

The following examples illustrate but do not limit in any way the invention.

EXAMPLE 1

This example presents the results from a stability study at 25° C. of a prior known acetate buffer solution containing the hydrobromide salt of HOOC-CH$_2$-(R)Cha-Pic-Nag in two different concentrations and having pH 5.0 at the beginning of the study.

(i) HOOC-CH$_2$-(R)Cha-Pic-Nag×2HBr buffer solution (0.04 mg/ml), pH 5

Composition:
HOOC-CH$_2$-(R)Cha-Pic-Nag×2HBr 0.04 mg
Sodium hydroxide 1M to pH 5 q.s.
Acetate buffer 0.05M (incl. NaCl, 9 mg ml) to 1 ml

| Stability Time (months) | pH | Temperature (°C.) | Degradation (area % of active compound) |
|---|---|---|---|
| 0 | 5.0 | 25 | — |
| 3 | 5.0 | 25 | 0.73 |
| 6 | — | 25 | 1.41 |
| 14 | 5.4 | 25 | 5.80 |

(ii) HOOC-CH$_2$-(R)Cha-Pic-Nag×2HBr buffer solution (9 mg/ml), pH 5

Composition:
HOOC-CH$_2$-(R)Cha-Pic-Nag×2HBr 9 mg
Sodium hydroxide 1M to pH 5 q.s.
Acetate buffer 0.05M (incl. NaCl, 9 mg/ml) to 1 ml

| Stability Time (months) | pH | Temperature (°C.) | Degradation (area % of active compound) |
|---|---|---|---|
| 0 | 5.0 | 25 | — |
| 6 | 5.2 | 25 | 1.70 |
| 14 | 5.3 | 25 | 3.68 |

Conclusion

This storage study indicates that storage at room temperature, 25° C., for 2 years will not be acceptable depending on the large amount of degradation of the active compound.

EXAMPLE 2

This example presents the results from a stability study at 25° C. of HOOC-CH$_2$-(R)Cha-Pic-Nag as a free base in the same concentration as Example 1 (ii) above, and starting at a pH about 5. The purpose of this study was to compare the stability of HOOC-CH$_2$-(R)Cha-Pic-Nag as a free base and as a salt thereof.

HOOC-CH$_2$-(R)Cha-Pic-Nag buffer solution (9 mg/ml), pH 5

Composition:
HOOC-CH$_2$-(R)Cha-Pic-Nag as free base 9 mg
Hydrochloric acid 1M to pH 5 q.s.
Acetate buffer 0.05M (incl. NaCl, 9 mg/ml) to 1 ml

| Stability Time (months) | pH | Temperature (°C.) | Degradation (area % of active compound) |
|---|---|---|---|
| 0 | 4.9 | 25 | — |
| 3 | 5.0 | 25 | 0.85 |
| 6 | 5.1 | 25 | 1.70 |
| 15 | 5.3 | 25 | 4.31 |

Conclusion

This study shows that there is no big difference in storage stability at room temperature. 25° C., by using HOOC-CH$_2$-(R)Cha-Pic-Nag as a salt or as a free base (cf. Example 1).

EXAMPLE 3

This example presents the result from a stability study at 25° C. of buffer solutions of HOOC-CH$_2$-(R)Cha-Pic-Nag at different pHs between 3 to 9.

(i) HOOC-CH$_2$-(R)Cha-Pic-Nag buffer solutions (9 mg/ml) at different pHs

Composition:
HOOC-CH$_2$-(R)Cha-Pic-Nag as free base 9 mg
Hydrochloric acid (1M) to pH q.s.
Acetate buffer 0.05M (incl. NaCl, 9 mg/ml) to 1 ml

| Stability Time (months) | pH | Temperature (°C.) | Degradation (area % of active compound) |
|---|---|---|---|
| 0 | 3.0 | 25 | — |
|   | 4.0 |    | — |
|   | 5.0 |    | — |
| 3 | 3.6 | 25 | 0.75 |
|   | 4.2 |    | 0.78 |
|   | 5.0 |    | 0.85 |
| 6 | 3.8 | 25 | 1.30 |
|   | 4.4 |    | 1.48 |
|   | 5.1 |    | 1.70 |

(ii) HOOC-CH$_2$-(R)Cha-Pic-Nag×2 HCl buffer solutions (1 mg/ml) pHs

Composition:
HOOC-CH$_2$-(R)Cha-Pic-Nag×2 HCl 1 mg
Buffer solution* to 1 ml* (for pH 4, 5 and 6 acetate buffer, for pH 8 phosphate buffer, for pH 9 carbonate buffer)

| Stability Time (months) | pH | Temperature (°C.) | Degradation (area % of active compound) |
|---|---|---|---|
| 3 | 4 | 25 | 1.1 |
|   | 5 | 25 | 1.3 |
|   | 6 | 25 | 2.4 |
|   | 8 | 25 | 10.8 |
|   | 9 | 25 | 12.2 |

Conclusion

This study shows that the degradation of HOOC-CH$_2$-(R)Cha-Pic-Nag decreases at lower pH, independently of base or salt form.

EXAMPLE 4

This example presents the result from a stability study at 25° C. of HOOC-CH$_2$-(R)Cha-Pic-Nag in two different concentrations at pH about 1.5, namely from 1.5 to 1.6.

HOOC-CH$_2$-(R)Cha-Pic-Nag water solution (0.4 mg/ml), pH 1.5

Composition:

HOOC-CH$_2$-(R)Cha-Pic-Nag as free base 0.4 mg

Hydrochloric acid 1M to pH 1.5 q.s.

Water to 1 ml

| Stability Time (months) | pH | Temperature (°C.) | Degradation (area % of active compound) |
|---|---|---|---|
| 0 | 1.5 | 25 | — |
| 3 | 1.5 | 25 | 0.27 |
| 6 | 1.6 | 25 | 0.58 |
| 12 | 1.6 | 25 | 1.36 |

(ii) HOOC-CH$_1$-(R)Cha-Pic-Nag water solution (66 mg/ml) pH 1.5
Composition:
HOOC-CH$_2$-(R)Cha-Pic-Nag as free base 66 mg
Hydrochloric acid 1M to pH 1.5 q.s.
Water to 1 ml

| Stability Time (months) | pH | Temperature (°C.) | Degradation (area % of active compound) |
|---|---|---|---|
| 0 | 1.6 | 25 | — |
| 3 | 1.6 | 25 | 0.31 |
| 6 | 1.6 | 25 | 0.65 |
| 12 | 1.8 | 25 | 1.40 |

Conclusion

This study shows that the degradation of HOOC-CH$_2$-(R)Cha-Pic-Nag decreases at this low pH.

EXAMPLE 5

This example presents the result from a stability study at 25° C. of HOOC-CH$_2$-(R)Cha-Pic-Nag in two different concentrations at pH 2.0. The purpose with this study is to compare the degradation of different pH in the range from 1.0 to 2.5 by comparing (i) with Example 4 (i).

(i) HOOC-CH$_2$-(R)Cha-Pic-Nag water solution (0.4 mg/ml), pH 2
Composition:
HOOC-CH$_2$-(R)Cha-Pic-Nag as free base 0.4 mg
Hydrochloric acid (1M) to pH 2 q.s.
Water to 1 ml

| Stability Time (months) | pH | Temperature (°C.) | Degradation (area % of active compound) |
|---|---|---|---|
| 0 | 2.0 | 25 | — |
| 3 | 2.0 | 25 | 0.46 |
| 6 | 2.0 | 25 | 0.91 |
| 12 | 2.2 | 25 | 2.05 |

(ii) HOOC-CH$_2$-(R)Cha-Pic-Nag water solution (26 mg/ml), pH 2
Composition:
HOOC-CH$_2$-(R)Cha-Pic-Nag as free base 26 mg
Hydrochloric acid 1M to pH 2 q.s.
Water to 1 ml

| Stability Time (months) | pH | Temperature (°C.) | Degradation (area % of active compound) |
|---|---|---|---|
| 0 | 2.1 | 25 | — |
| 3 | 2.1 | 25 | 0.45 |
| 6 | 2.1 | 25 | 0.94 |
| 12 | 2.4 | 25 | 1.93 |

Conclusion
This study shows that the degradation is decreased at this low pH.

EXAMPLE 6

This example presents the results from a stability study at 25° C. of HOOC-CH$_2$-(R)-Cgl-Aze-Pab as free base.

HOOC-CH$_2$-(R)-Cgl-Aze-Pab buffer solution (0.04 mg/ml), pH 6
Composition:
HOOC-CH$_2$-(R)-Cgl-Aze-Pab as free base 0.04 mg
Sodium hydroxide (1M) to pH 6 q.s.
Acetate buffer (0.05M) (incl. NaCl 9 mg/ml) to 1 ml

| Stability Time (months) | pH | Temperature (°C.) | Degradation (area % of active compound) |
|---|---|---|---|
| 0 | 5.9 | 25 | 1.07 |
| 1 | 5.9 | 25 | 1.30 |
| 3 | 6.0 | 25 | 1.50 |
| 6 | 6.0 | 25 | 2.10 |

Conclusion
This storage study shows that extended storage periods at 25° C. for this pH 6 formulation gives substantial degradation.

EXAMPLE 7

This example presents the result from a stability study at 25° C. of HOOC-CH$_2$-(R)-Cgl-Aze-Pab as buffer-solution and as water-solution, respectively, at different pHs.

HOOC-CH$_2$-(R)-Cgl-Aze-Pab buffer solutions (12.9 mg/ml) at different pHs
Composition:
(i) HOOC-CH$_2$-(R)-Cgl-Aze-Pab as a free base 12.9 mg
Hydrochloric acid 1M to pH q.s.
Acetate buffer 0.05M (incl. NaCl, 9 mg/ml) to 1 ml

| Stability Time (months) | pH | Temperature (°C.) | Degradation (area % of active compound) |
|---|---|---|---|
| 1 | 3.7 | 25 | 0.59 |
|   | 5.1 |    | 0.55 |
|   | 6.2 |    | 0.74 |
| 3 | 3.5 | 25 | 0.51 |
|   | 5.2 |    | 0.46 |
|   | 6.3 |    | 0.79 |
| 6 | 4.3 | 25 | 0.58 |
|   | 5.4 |    | 0.70 |
|   | 6.3 |    | 0.98 |

(ii) HOOC-CH$_2$-(R)-Cgl-Aze-Pab water solutions (12.9 mg/ml) at different pH

Composition:
HOOC-CH$_2$-(R)-Cgl-Aze-Pab as free base 12.9 mg
Hydrochloric acid 1M to pH q.s.
Water to 1 ml

| Stability Time (months) | pH | Temperature (°C.) | Degradation (area % of active compound) |
|---|---|---|---|
| 0 | 3.5 | 25 | 0.48 |
|  | 5.4 |  | 0.56 |
|  | 6.2 |  | 0.70 |
| 1 | 3.5 | 25 | 0.52 |
|  | 5.4 |  | 0.69 |
|  | 6.2 |  | 0.66 |
| 3 | 3.5 | 25 | 0.61 |
|  | 5.4 |  | 0.72 |
|  | 6.2 |  | 1.00 |

Conclusion

This study shows that the degradation of HOOC-CH$_2$-(R)-Cgl-Aze-Pab decreases at lower pH, with or without buffer systems.

EXAMPLE 8

This Example presents the result from a stability study at 50° C. of HOOC-CH$_2$-(R)-Cgl-Aze-Pab as water-solution, at different pHs.

HOOC-CH$_2$-(R)-Cgl-Aze-Pab water solutions (12.0 mg/ml) at different pHs
Composition:
(i) HOOC-CH$_2$-(R)-Cgl-Aze-Pab as a free base 12.0 mg
Hydrochloric acid 1M or NaOH 1M to pH q.s.
Water to 1 ml

| Stability Time (weeks) | pH | Temperature (°C.) | Major degradation product (area % active compound) |
|---|---|---|---|
| 0 | 2 | 50 | 0.57 |
|  | 4 |  | 0.42 |
|  | 7 |  | 0.44 |
|  | 9 |  | 2.41 |
| 2 | 2 | 50 | 0.47 |
|  | 4 |  | 0.48 |
|  | 7 |  | 3.31 |
|  | 9 |  | 25.6 |
| 4 | 2 | 50 | 0.50 |
|  | 4 |  | 0.58 |
|  | 7 |  | 6.76 |
|  | 9 |  | 33.8 |

Conclusion

This study shows that also at elevated temperature the degradation of HOOC-CH$_2$-(R)-Cgl-Aze-Pab decreases at lower pH.

Final conclusions

The studies above show that at room temperature, 25° C., the degradation of the active thrombin inhibitors HOOC-CH$_2$(R)Cha-Pic-Nag and HOOC-CH$_2$-(R)-Cgl-Aze-Pab, respectively, independently as a free base or as a salt and independently of concentration of active compound, decreases at lower pH.

Furthermore, the studies show that water solutions of said thrombin inhibitors having a pH in the range from 1.0 to 2.5, are more storage stable at room temperature for extended periods.

ABBREVIATIONS
Aze=(S)-Azetidine-2-carboxylic acid
Cgl=(S)-Cyclohexyl glycine
Cha=(S)-β-cyclohexyl alanine
Nag=noragmatine
Pab=1-amidino-4-aminomethyl benzene
Pic=(S)-pipecolinic acid

We claim:

1. A storage stable concentrated water solution for infusion having a pH in the range from 1.0 to 2.5 and containing an active thrombin inhibitor having the formula

HOOC-CH$_2$-Y wherein Y is (R)-Cha-Pic-Nag or (R)-Cgl-Aze-Pab, as a salt or as a free base thereof.

2. The solution according to claim 1 wherein the thrombin inhibitor is HOOC-CH$_2$-(R)-Cha-Pic-Nag as the free base.

3. The solution according to claim 1 the thrombin inhibitor is HOOC-CH$_2$-(R)-Cgl-Aze-Pab as the free base.

4. The solution according to claim 1 wherein the pH is from 1.5 to 2.0.

5. The solution according to any one of the claims 1, 2 or 4 wherein the concentration of active thrombin inhibitor is between 0.001 to 200 mg/ml.

6. The solution according to any one of the claims 1, 3 or 4 wherein the concentration of active thrombin inhibitor is between 0.001 to 300 mg/ml.

7. The solution according to any one of the claims 1, 2, or 4 consisting of the active compound HOOC-CH$_2$-(R)-Cha-Pic-Nag, water and an inorganic mineral acid.

8. The solution according to any of the claims 1, 3, or 4 consisting of the active compound HOOC-CH$_2$-(R)-Cgl-Aze-Pab, water and an inorganic mineral acid.

9. The solution according to claim 7, wherein the inorganic mineral acid is hydrochloric acid.

10. The solution according to claim 1, in which after storage at room temperature for at least two years at least 95% of the active compound remains.

11. A process for preparing a storage stabil concentrated water solution according to claim 1 which comprises dissolving the active thrombin inhibitor in water, adjusting of the solution pH to the range 1.0 to 2.5.

12. A process according to claim 11, wherein hydrochloric acid is used to adjust pH.

13. A method for the treatment of a patient in need of a thrombin inhibitor by administration intravenously by infusion the storage stable concentrated water-solution according to any one of claim 1.

14. A method for stabilizing an active thrombin inhibitor having the formula

HOOC-CH$_2$-Y wherein Y is (R)-Cha-Pic-Nag or (R)-Cgl-Aze-Pab, as a salt or as a free base thereof, comprising dissolving said thrombin inhibitor in water and adjusting the obtained solution with a physiologically acceptable organic or inorganic acid for obtaining a pH from 1.0 to 2.5.

15. A solution according to claim 5 consisting of the active compound HOOC-CH$_2$-(R)-Cha-Pic-Nag, water and an inorganic mineral acid.

16. The solution according to claim 6 consisting of the active compound HOOC-CH$_2$-(R)-Cgl-Aze-Pab, water and an inorganic mineral acid.

17. The solution according to claim 8, wherein the inorganic mineral acid is hydrochloric acid.

* * * * *